United States Patent
De Matos Gomes et al.

(10) Patent No.: US 12,332,331 B2
(45) Date of Patent: Jun. 17, 2025

(54) PULSE SEQUENCES AND FREQUENCY SWEEP PULSES FOR SINGLE-SIDED MAGNETIC RESONANCE IMAGING

(71) Applicant: PROMAXO, INC., Oakland, CA (US)

(72) Inventors: Muller Francis De Matos Gomes, Hayward, CA (US); Aleksandar Nacev, San Francisco, CA (US)

(73) Assignee: Promaxo, Inc., Oakland, CA (US)

( * ) Notice: Subject to any disclaimer, the term of this patent is extended or adjusted under 35 U.S.C. 154(b) by 74 days.

(21) Appl. No.: 17/905,716

(22) PCT Filed: Mar. 9, 2021

(86) PCT No.: PCT/US2021/021461
§ 371 (c)(1),
(2) Date: Sep. 6, 2022

(87) PCT Pub. No.: WO2021/183482
PCT Pub. Date: Sep. 16, 2021

(65) Prior Publication Data
US 2023/0296707 A1    Sep. 21, 2023

Related U.S. Application Data

(60) Provisional application No. 62/987,286, filed on Mar. 9, 2020.

(51) Int. Cl.
*G01R 33/36* (2006.01)
*A61B 5/055* (2006.01)
(Continued)

(52) U.S. Cl.
CPC .......... *G01R 33/3607* (2013.01); *A61B 5/055* (2013.01); *G01R 33/445* (2013.01);
(Continued)

(58) Field of Classification Search
CPC .......................... G01R 33/445; G01R 33/3607
See application file for complete search history.

(56) References Cited

U.S. PATENT DOCUMENTS

| 4,801,884 A | 1/1989 | Oppelt et al. |
| 4,893,081 A | 1/1990 | Zur |

(Continued)

FOREIGN PATENT DOCUMENTS

| CN | 103976735 A | 8/2014 |
| JP | H05507210 A | 10/1993 |

(Continued)

OTHER PUBLICATIONS

International Search Report and Written Opinion for International PCT Application No. PCT/US2021/021461, dated Jun. 14, 2021.

(Continued)

*Primary Examiner* — Gregory H Curran
(74) *Attorney, Agent, or Firm* — WILSON SONSINI GOODRICH & ROSATI

(57) ABSTRACT

Single-sided MRI scanners, systems, and methods are disclosed. A method can include applying a first sweeping frequency pulse defining an X axis; applying a second sweeping frequency pulse defining a Y axis; applying a third sweeping frequency pulse defining the Y axis; and applying a fourth sweeping frequency pulse defines a −X axis. The sweep rate of the fourth sweeping frequency pulse can be less than the sweep rate of the third and/or second sweeping frequency pulse. The sweeping frequency pulses can be chirp pulses. Frequency sweep DEFT pulse sequences can provide the benefits of a broader bandwidth and less sensitivity to the inhomogeneity of a single-sided MRI scanner.

23 Claims, 9 Drawing Sheets

(51) Int. Cl.
*G01R 33/38* (2006.01)
*G01R 33/44* (2006.01)
*G01R 33/483* (2006.01)

(52) U.S. Cl.
CPC ...... *G01R 33/3802* (2013.01); *G01R 33/3808* (2013.01); *G01R 33/483* (2013.01)

(56) References Cited

U.S. PATENT DOCUMENTS

| | | | |
|---|---|---|---|
| 5,303,705 | A | 4/1994 | Nenov |
| 5,320,099 | A | 6/1994 | Roberts et al. |
| 5,448,170 | A | 9/1995 | Bodenhausen et al. |
| 6,054,853 | A | 4/2000 | Miyamoto et al. |
| 9,513,358 | B2 * | 12/2016 | Levin ................ G01R 33/5602 |
| 10,234,524 | B2 * | 3/2019 | Zeller ................ G01R 33/5611 |
| D895,803 | S | 9/2020 | Nacev et al. |
| D942,012 | S | 1/2022 | Nacev et al. |
| 11,506,737 | B2 | 11/2022 | Gomes |
| D980,981 | S | 3/2023 | Nacev et al. |
| 11,609,291 | B2 | 3/2023 | Nacev et al. |
| 11,656,303 | B2 | 5/2023 | Nacev et al. |
| 11,921,178 | B2 | 3/2024 | De Matos Gomes |
| 2018/0356480 | A1 | 12/2018 | Weinberg et al. |
| 2022/0113361 | A1 | 4/2022 | Nacev et al. |
| 2022/0146613 | A1 | 5/2022 | Gomes |
| 2022/0342020 | A1 | 10/2022 | Narayanan et al. |
| 2023/0104153 | A1 | 4/2023 | Gomes et al. |
| 2023/0106912 | A1 | 4/2023 | Kumar et al. |
| 2023/0109705 | A1 | 4/2023 | De Matos Gomes |
| 2023/0110217 | A1 | 4/2023 | Nacev et al. |

FOREIGN PATENT DOCUMENTS

| | | |
|---|---|---|
| JP | 2004166751 A | 6/2004 |
| JP | 2004313276 A | 11/2004 |
| WO | 2014203253 A1 | 12/2014 |
| WO | WO-2020168233 A1 | 8/2020 |
| WO | WO-2020172672 A1 | 8/2020 |
| WO | WO-2020172673 A1 | 8/2020 |
| WO | WO-2020198395 A1 | 10/2020 |
| WO | WO-2020198396 A1 | 10/2020 |
| WO | WO-2020264194 A1 | 12/2020 |
| WO | WO-2021150902 A1 | 7/2021 |
| WO | WO-2021168291 A2 | 8/2021 |
| WO | 2021183482 A1 | 9/2021 |
| WO | WO-2021183484 A1 | 9/2021 |

OTHER PUBLICATIONS

Stockman et al., Transmit Array Spatial Encoding (TRASE) using broadband WURST pulses for RF spatial encoding in inhomogeneous Bo fields, Journal of Magnetic Resonance (Apr. 8, 2016), 268:36-48.

Cooley et al., Two-Dimensional Imaging in a Lightweight Portable MRI Scanner without Gradient Coils, Magnetic Resonance in Medicine (2015), 73:872-883.

Dumez et al., Multidimensional excitation pulses based on spatiotemporal encoding concepts, Journal of Magnetic Resonance (Nov. 7, 2012), 226:22-34.

Tal et al., Spatial encoding and the single-scan acquisition of high definition MR images in inhomogeneous fields, Journal of Magnetic Resonance (Jul. 14, 2006), 182:179-194.

JP Serial No. 2022-554409 Office Action dated Sep. 3, 2024.

PCT/US2021/021461 International Preliminary Report on Patentability dated Sep. 6, 2022.

JP2022-554409 Office Action dated Apr. 10, 2025, and an English translation.

* cited by examiner

PULSE SEQUENCES AND FREQUENCY SWEEP PULSES FOR SINGLE-SIDED MAGNETIC RESONANCE IMAGING

CROSS-REFERENCE TO RELATED APPLICATIONS

This application is a U.S. National Stage Entry under 35 U.S.C. § 371 of International Patent Application No. PCT/US2021/021461, entitled PULSE SEQUENCES AND FREQUENCY SWEEP PULSES FOR SINGLE-SIDED MAGNETIC RESONANCE IMAGING, filed Mar. 9, 2021, which claims the benefit under 35 U.S.C. § 119 (e) to U.S. Provisional Patent Application No. 62/987,286, titled SYSTEMS AND METHODS FOR ADAPTING DRIVEN EQUILIBRIUM FOURIER TRANSFORM FOR SINGLE-SIDED MRI, filed Mar. 9, 2020, the entire disclosures of which are hereby incorporated by reference herein.

BACKGROUND

In single-sided magnetic resonance imaging (MRI) scans, the magnetic field generated by the magnet is inhomogeneous in the field of view. Under these conditions, images generated by the MRI system can show inadequate contrast or Signal-to-Noise ratio (SNR).

Driven Equilibrium Fourier Transform (DEFT) is a radio frequency (RF) pulse sequence in which the equilibrium magnetization of nuclei with long T1 is restored rapidly by recycling transverse magnetization. By driving the equilibrium, it is possible to rapidly image without sacrificing SNR.

SUMMARY

In one aspect of the present disclosure, a method for transmitting radio frequency pulses for a single-sided magnetic imaging apparatus, comprises: applying a first sweeping frequency pulse having a first duration and a first sweep rate, wherein the first sweeping frequency pulse defines an X axis; applying a second sweeping frequency pulse having a second duration and a second sweep rate, wherein the second sweeping frequency pulse defines a first Y axis; applying a third sweeping frequency pulse having a third duration and a third sweep rate, wherein the third sweeping frequency pulse defines a second Y axis; and applying a fourth sweeping frequency pulse having a fourth duration and a fourth sweep rate, wherein the fourth sweeping frequency pulse defines a –X axis, and wherein the fourth sweep rate is less than the third sweep rate.

In another aspect of the present disclosure, a magnetic imaging apparatus, comprises: a permanent magnet comprising a face; a gradient coil set; an electromagnet; and a radio frequency coil, wherein an inherent gradient magnetic field extends from the magnetic imaging apparatus relative to a first axis into the field of view, wherein the first axis is perpendicular to the face of the permanent magnet. The magnetic imaging apparatus further comprises a control circuit configured to control the radio frequency coil to: apply a first sweeping frequency pulse having a first duration and a first sweep rate, wherein the first sweeping frequency pulse defines a second axis that is orthogonal to the first axis; apply a second sweeping frequency pulse having a second duration and a second sweep rate, wherein the second sweeping frequency pulse defines a third axis that is orthogonal to the first axis and to the second axis; apply a third sweeping frequency pulse having a third duration and a third sweep rate, wherein the third sweeping frequency pulse defines the third axis; and apply a fourth sweeping frequency pulse having a fourth duration and a fourth sweep rate, wherein the fourth sweeping frequency pulse defines the negative second axis, wherein the fourth sweep rate is less than the third sweep rate.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings.

Figure 2:
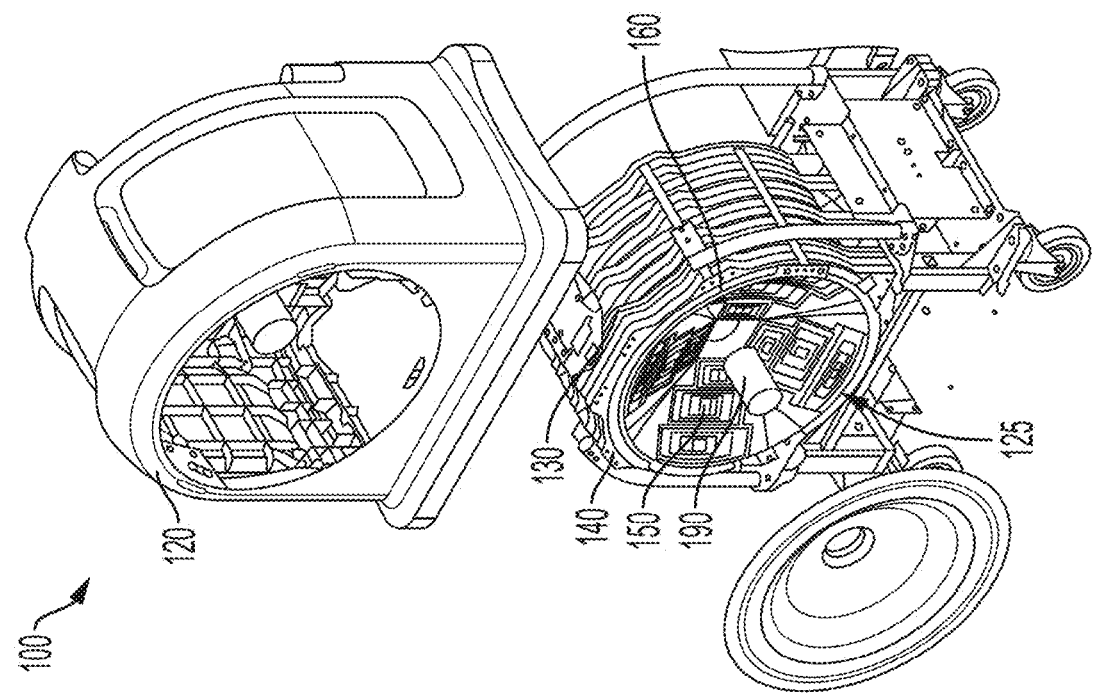
FIG. 2 is an exploded, perspective view of the MRI scanner of FIG. 1, in which the permanent magnet assembly and the gradient coil sets within the housing are exposed, according to various aspects of the present disclosure.

The accompanying drawings are not intended to be drawn to scale. Corresponding reference characters indicate corresponding parts throughout the several views. For purposes of clarity, not every component may be labeled in every drawing. The exemplifications set out herein illustrate certain embodiments of the invention, in one form, and such exemplifications are not to be construed as limiting the scope of the invention in any manner.

DETAILED DESCRIPTION

Applicant also owns International Patent Application titled PHASE ENCODING WITH FREQUENCY SWEEP PULSES FOR MAGNETIC RESONANCE IMAGING IN INHOMOGENEOUS MAGNETIC FIELDS, filed Mar. 9, 2021, which claims priority to U.S. Provisional Patent Application No. 62/987,292, titled SYSTEMS AND METHODS FOR LIMITING k-SPACE TRUNCATION IN A SINGLE-SIDED MRI SCANNER, filed Mar. 9, 2020, both of which are incorporated by reference herein in their respective entireties.

The following international patent applications are incorporated by reference herein in their respective entireties:

International Application No. PCT/US2020/018352, titled SYSTEMS AND METHODS FOR ULTRALOW FIELD RELAXATION DISPERSION, filed Feb. 14, 2020, now International Publication No. WO2020/168233;

International Application No. PCT/US2020/019530, titled SYSTEMS AND METHODS FOR PERFORMING MAGNETIC RESONANCE IMAGING, filed Feb. 24, 2020, now International Publication No. WO2020/172673;

International Application No. PCT/US2020/019524, titled PSEUDO-BIRDCAGE COIL WITH VARIABLE TUNING AND APPLICATIONS THEREOF, filed Feb. 24, 2020, now International Publication No. WO2020/172672;

International Application No. PCT/US2020/024776, titled SINGLE-SIDED FAST MRI GRADIENT FIELD COILS AND APPLICATIONS THEREOF, filed Mar. 25, 2020, now International Publication No. WO2020/198395;

International Application No. PCT/US2020/024778, titled SYSTEMS AND METHODS FOR VOLUMETRIC ACQUISITION IN A SINGLE-SIDED MRI SYSTEM, filed Mar. 25, 2020, now International Publication No. WO2020/198396;

International Application No. PCT/US2020/039667, title SYSTEMS AND METHODS FOR IMAGE RECONSTRUCTIONS IN MAGNETIC RESONANCE IMAGING, filed Jun. 25, 2020, now International Publication No. WO2020/264194;

International Application No. PCT/US2021/014628, titled MRI-GUIDED ROBOTIC SYSTEMS AND METHODS FOR BIOPSY, filed Jan. 22, 2021; and International Application No. PCT/US2021/018834, titled RADIO FREQUENCY RECEPTION COIL NETWORKS FOR SINGLE-SIDED MAGNETIC RESONANCE IMAGING, filed Feb. 19, 2021.

U.S. Patent Application Publication No. 2018/0356480, titled UNILATERAL MAGNETIC RESONANCE IMAGING SYSTEM WITH APERTURE FOR INTERVENTIONS AND METHODOLOGIES FOR OPERATING SAME, published Dec. 13, 2018, is incorporated by reference herein in its entirety.

Before explaining various aspects of an MRI system and methods in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

In accordance with various aspects, an MRI system is provided that can include a unique imaging region that can be offset from the face of a magnet. Such offset and single-sided MRI systems are less restrictive as compared to traditional MRI scanners. In addition, this form factor can have a built-in or inherent magnetic field gradient that creates a range of magnetic field values over the region of interest. In other words, the inherent magnetic field can be inhomogeneous. The inhomogeneity of the magnetic field strength in the region of interest for the single-sided MRI system can be more than 200 parts per million (ppm). For example, the inhomogeneity of the magnetic field strength in the region of interest for the single-sided MRI system can between 200 ppm and 200,000 ppm. In various aspects of the present disclosure, the inhomogeneity in the region of interest can be greater than 1,000 ppm and can be greater than 10,000 ppm. In one instance, the inhomogeneity in the region of interest can be 81,000 ppm.

The inherent magnetic field gradient can be generated by a permanent magnet within the MRI scanner. The magnetic field strength in the region of interest for the single-sided MRI system can be less than 1 Tesla (T), for example. For example, the magnetic field strength in the region of interest for the single-sided MRI system can be less than 0.5 T. In other instances, the magnetic field strength can be greater than 1 T and may be 1.5 T, for example. This system can operate at a lower magnetic field strength as compared to typical MRI systems allowing for a relaxation on the RX coil design constraints and/or allowing for additional mechanisms, like robotics, for example, to be used with the MRI scanner. Exemplary MRI-guided robotic systems are further described in International Application No. PCT/US2021/014628, titled MRI-GUIDED ROBOTIC SYSTEMS AND METHODS FOR BIOPSY, filed Jan. 22, 2021, for example.

As stated above, DEFT is an RF pulse sequence in which the equilibrium magnetization of nuclei with long T1 is restored rapidly by recycling transverse magnetization. By driving the equilibrium, it is possible to rapidly image without sacrificing SNR. In a homogenous magnetic field, a DEFT pulse sequence comprises an excitation RF pulse that is configured to rotate the magnetic field from a longitudinal axis extending from the primary magnet assembly (e.g. a permanent magnet) into a transverse plane, followed by a refocusing RF pulse that is configured to rephase the magnetic field from the transverse plane back to the longitudinal axis. DEFT works similarly to balanced steady state free precession sequences, for example.

In single-sided MRI systems, the magnetic field generated by the magnet can be very inhomogeneous (e.g. approximately 81,000 ppm). Under these conditions, images generated by the MRI system can show inadequate contrast or SNR.

Systems and methods for effectively collecting nuclear magnetic resonance spectra and magnetic resonance images in inhomogeneous fields are described herein. Inhomogeneous fields, such as those resulting from a single-sided MRI scanner, can cause increased phase dispersion upon rotating the magnetic field into a transverse plane relative to the longitudinal axis that extends from the single-sided MRI scanner and permanent magnet thereof into the region of interest. The phase dispersion should be minimized. For example, an improved DEFT pulse sequence for a single-sided MRI and other inhomogeneous magnetic fields can adjust the phase dispersion and improve contrast or SNR. In various instances, higher quality images can be collected in less time.

Initially, magnetization at thermal equilibrium (M) lies along a longitudinal axis, or Z axis, extending from the single-sided MRI scanner into the region of interest. Application of a first RF excitation pulse (e.g. a first 90 degree pulse) along the Y axis causes M to tip into the X-Y plane. For single-sided MRI scanners and other inhomogeneous fields, the inhomogeneity will then cause the magnetization to dephase. This dephasing can be refocused with a first refocusing RF pulse (e.g. a first 180 degree pulse) to form an echo. After the first refocusing RF pulse, the magnetization can be refocused again with a second RF refocusing pulse (e.g. a second 180 degree pulse), and then second excitation RF pulse (e.g. a second 90 degree driven equilibrium pulse), which brings the remaining magnetization back to the Z axis. Without the second 90 degree pulse, the magnetization would decay as a result of spin-spin relaxation T2 and the inhomogeneous broadening T2*. With the second 90 excitation RF pulse, the remaining transverse magnetization is preserved in the Z axis, which speeds up the signal recovery.

DEFT is commonly used in systems with homogeneous fields and with conventional or single frequency RF pulses. A single frequency RF pulse can also be referred to as "hard" pulse. Adapting DEFT to single-sided MRI systems and inhomogeneous fields can require that the bandwidth of the RF pulses used in the DEFT sequence be expanded. In accordance with various aspects, frequency sweep RF pulses, or chirp pulses, can be used instead of single frequency RF pulses. By collecting data with a frequency sweep DEFT sequence, higher quality images can be collected in less time when compared to single echo chirped sequences.

Figure 1:
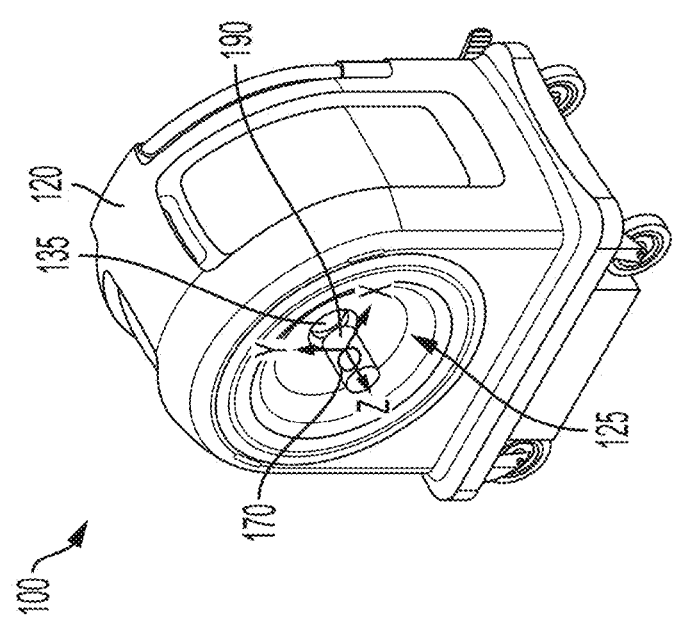
FIG. 1 is a perspective view of an MRI scanner, according to various aspects of the present disclosure.

FIGS. 1-6 depict an MRI scanner 100 and components thereof. As shown in FIGS. 1 and 2, the MRI scanner 100 includes a housing 120 having a face or front surface 125, which is concave and recessed. In other aspects, the face of the housing 120 can be flat and planar. The front surface 125 can face the object being imaged by the MRI scanner. As shown in FIGS. 1 and 2, the housing 120 includes a permanent magnet assembly 130, an RF transmission coil (TX) 140, a gradient coil set 150, an electromagnet 160, and a RF reception coil (RX) 170. In other instances, the housing 120 may not include the electromagnet 160. Moreover, in certain instances, the RF reception coil 170 and the RF transmission coil 140 can be incorporated into a combined Tx/Rx coil array.

Figure 4:
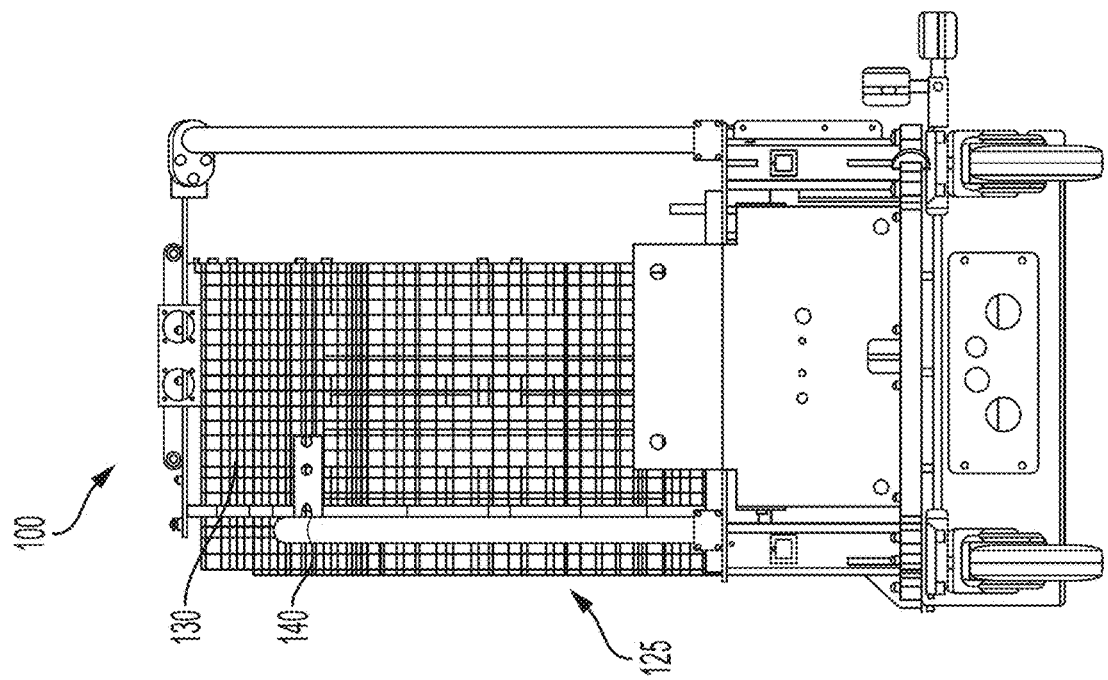
FIG. 4 is an elevation view of the MRI scanner of FIG. 1, according to various aspects of the present disclosure.
Figure 3:
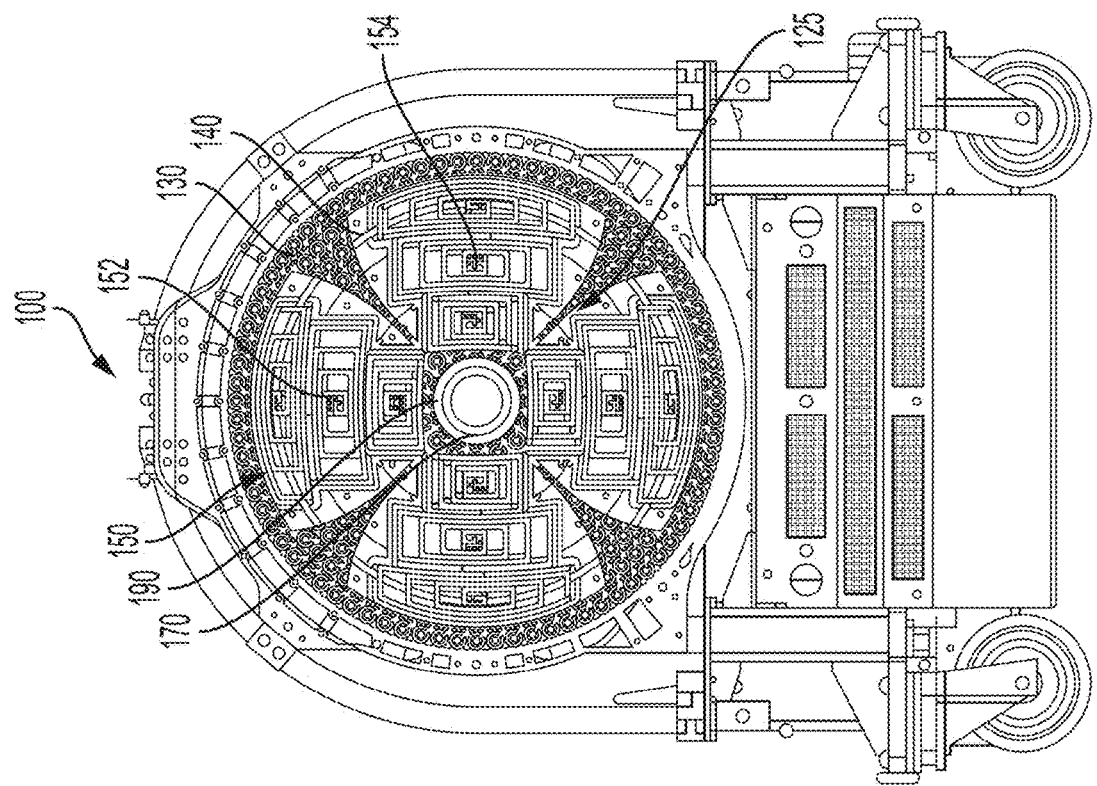
FIG. 3 is an elevation view of the MRI scanner of FIG. 1, according to various aspects of the present disclosure.
Figure 5:
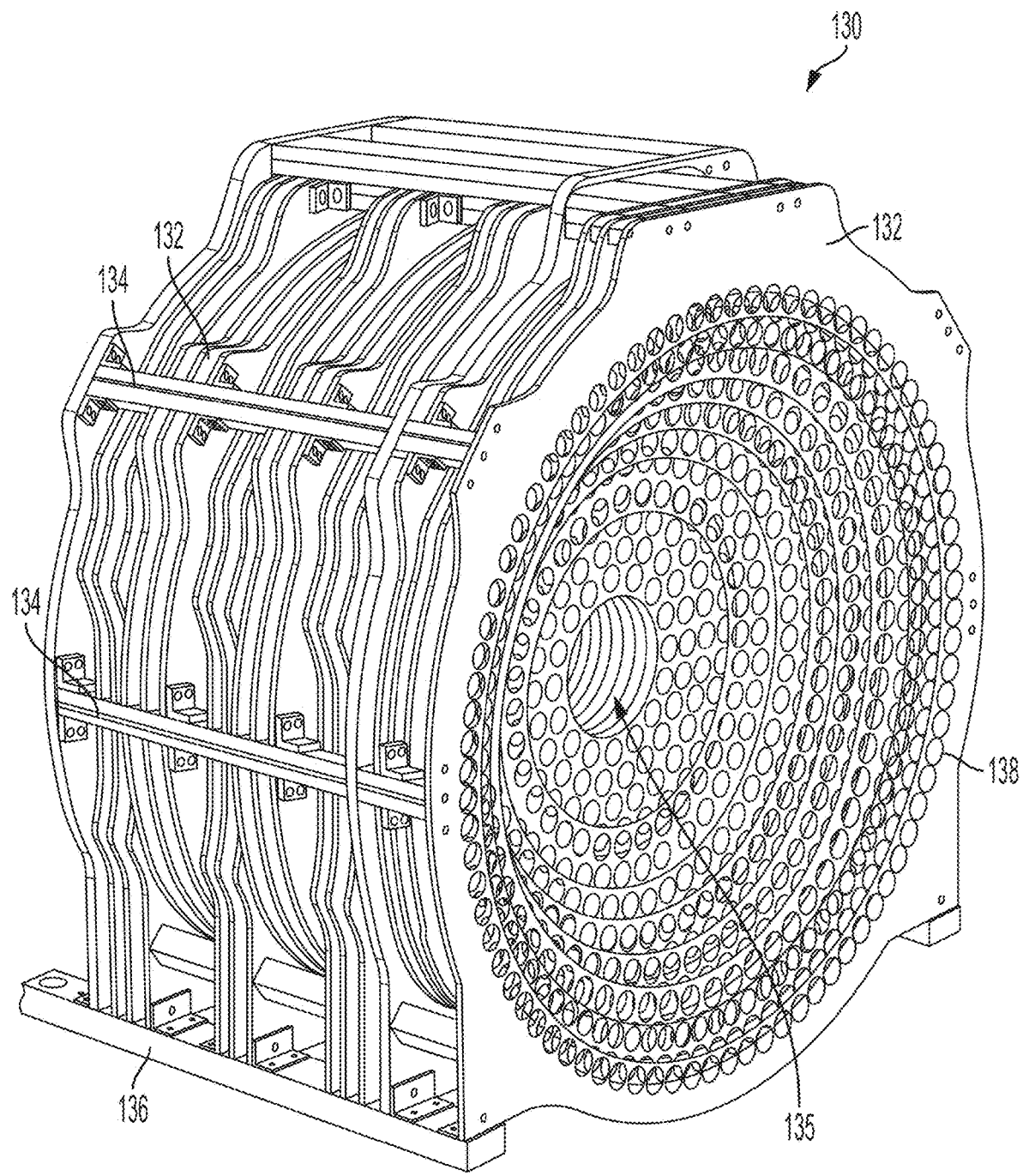
FIG. 5 is a perspective view of the permanent magnet assembly of the MRI scanner of FIG. 1, according to various aspects of the present disclosure.
Figure 6:
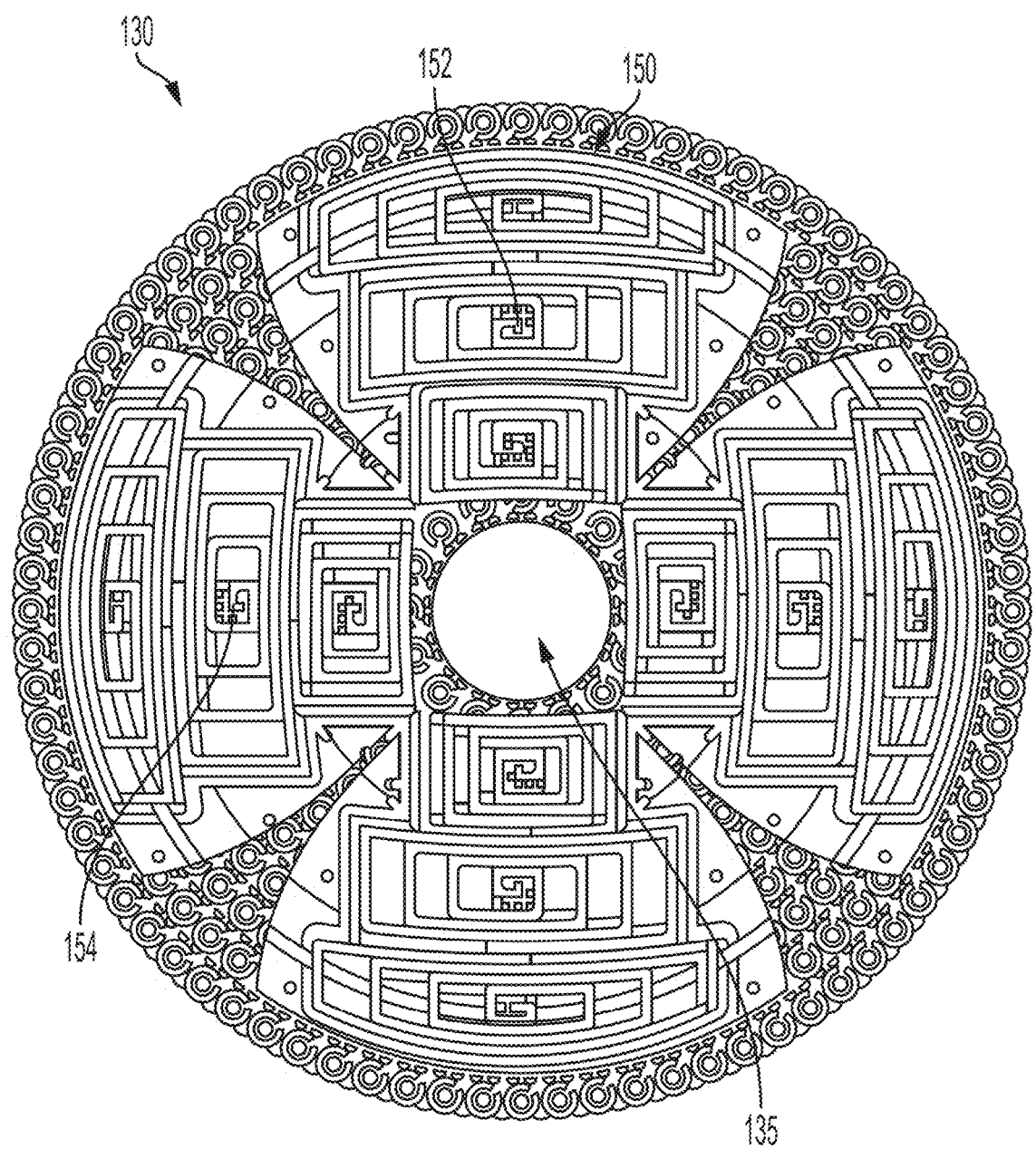
FIG. 6 is an elevation view of the gradient coil set and the permanent magnet assembly of the MRI system shown in FIG. 1, according to various aspects of the present disclosure.

Referring primarily to FIGS. 3-5, the permanent magnet assembly 130 includes an array of magnets. The array of magnets forming the permanent magnet assembly 130 are configured to cover the front surface 125, or patient-facing surface, of the MRI scanner 100 (see FIG. 3) and are shown as horizontal bars in FIG. 4. The permanent magnet assembly 130 includes a plurality of cylindrical permanent magnets in a parallel configuration. Referring primarily to FIG. 5, the permanent magnet assembly 130 comprises parallel plates 132 that are held together by brackets 134. The system can be attached to the housing 120 of the MRI scanner 100 at a bracket 136. There can be a plurality of holes 138 in the parallel plates 132. The permanent magnet assembly 130 can include any suitable magnetic materials, including but not limited to rare-earth based magnetic materials, such as for example, Neodymium-based magnetic materials, for example.

The permanent magnet assembly 130 defines an access aperture or bore 135, which can provide access to the patient through the housing 120 from the opposite side of the housing 120. In other aspects of the present disclosure, the array of permanent magnets forming a permanent magnet assembly in the housing 120 may be bore-less and define an uninterrupted or contiguous arrangement of permanent magnets without a bore defined therethrough. In still other instances, the array of permanent magnets in the housing 120 may form more than one bore/access aperture therethrough.

In accordance with various aspects of the present disclosure, the permanent magnet assembly 130 provides a magnetic field B0 in a region of interest 190 that is along the Z axis, shown in FIG. 1. The Z axis is perpendicular to the permanent magnet assembly 130. Stated differently, the Z axis extends from a center of the permanent magnet assembly 130 and defines a direction of the magnetic field B0 away from the face of the permanent magnet assembly 130. The Z axis can define the primary magnetic field B0 direction. The primary magnetic field B0 can decrease along the Z axis, i.e. an inherent gradient, farther from the face of the permanent magnet assembly 130 and in the direction indicated with the arrow in FIG. 1.

In one aspect, the inhomogeneity of the magnetic field in the region of interest 190 for the permanent magnet assembly 130 can be approximately 81,000 ppm. In another aspect, the inhomogeneity of the magnetic field strength in the region of interest 190 for the permanent magnet assembly 130 can be between 200 ppm to 200,000 ppm and can be greater than 1,000 ppm in certain instances, and greater than 10,000 ppm in various instances.

In one aspect, the magnetic field strength of the permanent magnet assembly 130 can be less than 1 T. In another aspect, the magnetic field strength of the permanent magnet assembly 130 can be less than 0.5 T. In other instances, the magnetic field strength of the permanent magnet assembly 130 can be greater than 1 T and may be 1.5 T, for example. Referring primarily to FIG. 1., the Y axis extends up and down from the Z axis and the X axis extends to the left and right from the Z axis. The X axis, the Y axis, and the Z axis are all orthogonal to one another and the positive direction of each axis is indicated by the corresponding arrow in FIG. 1.

The RF transmission coils 140 are configured to transmit RF waveforms and associated electromagnetic fields. The RF pulses from the RF transmission coils 140 are configured to rotate the magnetization produced by the permanent magnet 130 by generating an effective magnetic field, referred to as B1, that is orthogonal to the direction of the permanent magnetic field (e.g. an orthogonal plane).

Referring primarily to FIG. 3, the gradient coil set 150 includes two sets of gradient coils 152, 154. The sets of gradient coils 152, 154 are positioned on the face or front surface 125 of the permanent magnet assembly 130 intermediate the permanent magnet assembly 130 and the region of interest 190. Each set of gradient coils 152, 154 includes a coil portion on opposing sides of the bore 135. Referring to the axes in FIG. 1, the gradient coil set 154 may be the gradient coil set corresponding to the X axis, for example, and the gradient coil set 152 may be the gradient coil set corresponding to the Y axis, for example. The gradient coils 152, 154 can enable encoding along the X axis and Y axis, as further described in PHASE ENCODING WITH FREQUENCY SWEEP PULSES FOR MAGNETIC RESONANCE IMAGING IN INHOMOGENEOUS MAGNETIC FIELDS, filed Mar. 9, 2021 and U.S. Provisional Patent Application No. 62/987,292, titled SYSTEMS AND METHODS FOR LIMITING K-SPACE TRUNCATION IN A SINGLE-SIDED MRI SCANNER, filed Mar. 9, 2020, both of which are incorporated by reference herein in their respective entireties.

Figure 7:
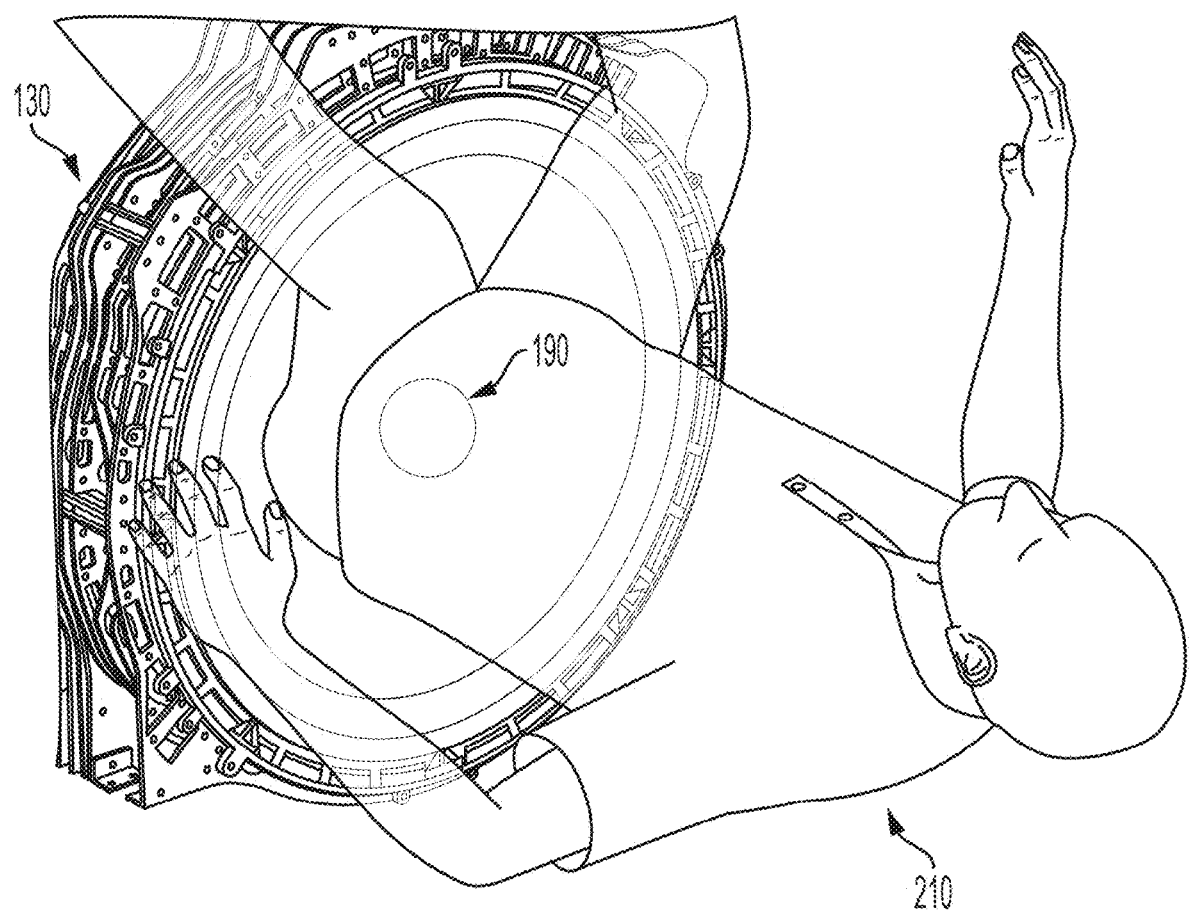
FIG. 7 illustrates exemplary positioning of a patient for imaging by a single-sided MRI scanner for certain surgical procedures and interventions, according to various aspects of the present disclosure.

In accordance with various aspects, using the MRI scanner 100 illustrated in FIGS. 1-6, a patient can be positioned in any number of different positions depending on the type of anatomical scan. FIG. 7 shows an example where the pelvis is scanned with the MRI scanner 100. To perform the scan a patient 210 can be laid on a surface in a lithotomy position. As illustrated in FIG. 7, for the pelvic scan, the patient 210 can be positioned to have their back resting on a table and legs raised up to be resting against the top of the scanner 100. The pelvic region can be positioned directly in front of the permanent magnet assembly 130 and the bore 135 and the region of interest 190 is in the pelvic region of the patient 210.

Figure 8:
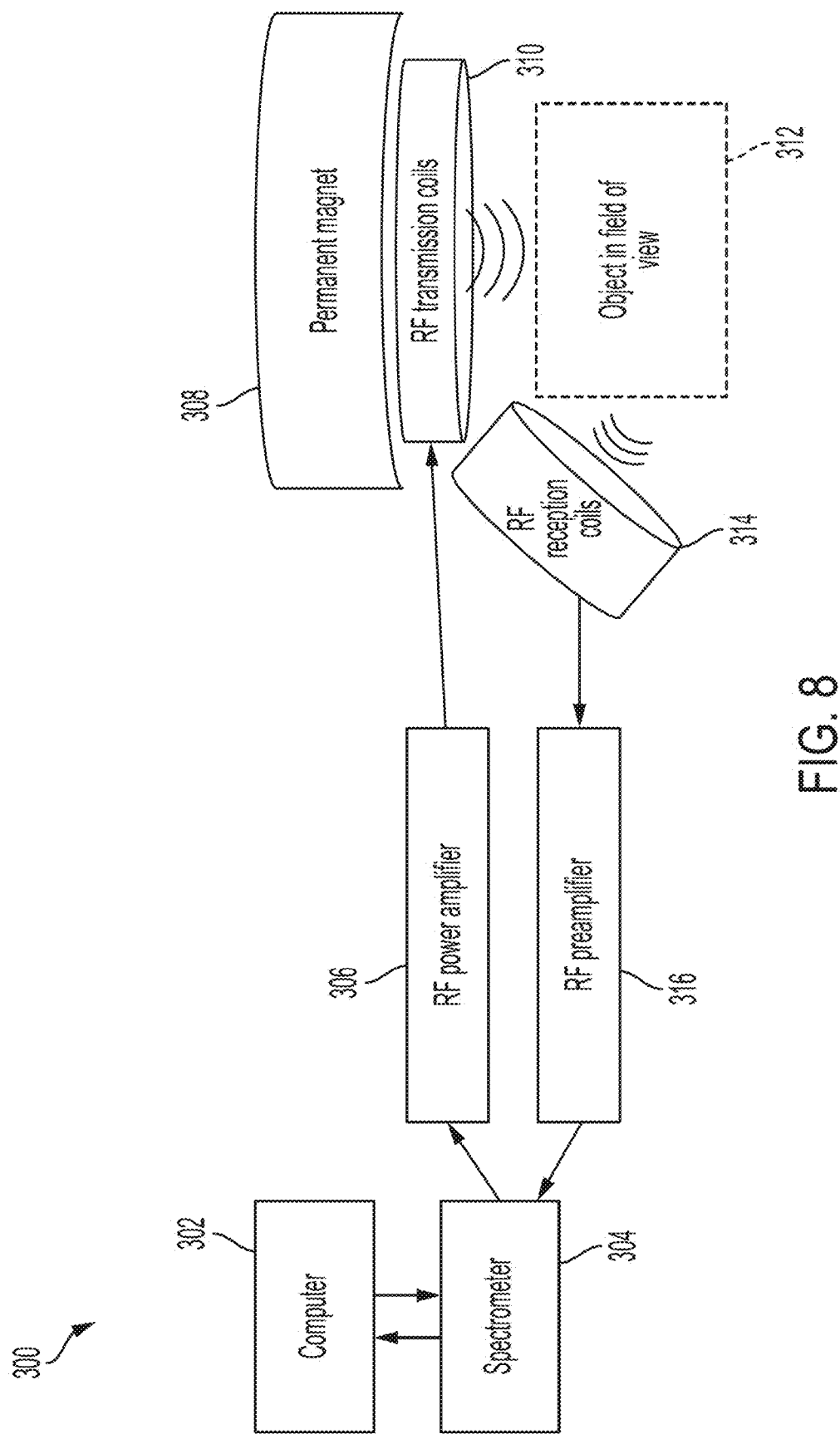
FIG. 8 is a control schematic for a single-sided MRI system, according to various aspects of the present disclosure.

Referring now to FIG. 8, a control schematic for a single-sided MRI system 300 is shown. The single-sided MRI scanner 100 and/or components thereof (FIGS. 1-6) can be incorporated into the MRI system 300 in various aspects of the present disclosure. For example, the imaging system 300 includes a permanent magnet assembly 308, which can be similar to the permanent magnet assembly 130 (see FIGS. 2-5) in various instances. The imaging system 300 also includes RF transmission coils 310, which can be similar to the RF transmission coil 140 (see FIG. 3), for example. Moreover, the imaging system 300 includes RF reception coils 314, which can be similar to the RF reception coils 170 (see FIG. 3), for example. In various aspects, the RF transmission coils 310 and/or the RF reception coils can also be positioned in the housing of an MRI scanner and, in certain instances, the RF transmission coils 310 and the RF reception coils 314 can be combined into integrated Tx/Rx coils.

The single-sided MRI system 300 also includes a computer 302, which is in signal communication with a spectrometer 304, and is configured to send and receive signals between the computer 302 and the spectrometer 304.

The main magnetic field B0 generated by the permanent magnet 308 extends away from the permanent magnet 308 and away from the RF transmission coils 310 into the field of view 312. The field of view 312 contains an object that is being imaged by the MRI system 300.

During the imaging process, the main magnetic field B0 extends into the field of view 312. The direction of the effective magnetic field (B1) changes in response to the RF pulses and associated electromagnetic fields from the RF transmission coils 310. For example, the RF transmission coils 310 are configured to selectively transmit RF signals or pulses to an object in the field of view, e.g. tissue. These RF pulses alter the effective magnetic field experienced by the spins in the sample (e.g. patient tissue). When the RF pulses are on, the effective field experienced by spins on resonance is solely the RF pulse, effectively canceling the static B0 field. The RF pulses can be chirp or frequency sweep pulses, for example, as further described herein.

Moreover, when the object in the field of view 312 is excited with RF pulses from the RF transmission coils 310, the precession of the object results in an induced electric current, or MR current, which is detected by the RF reception coils 314. The RF reception coils 314 can send the excitation data to an RF preamplifier 316. The RF preamplifier 316 can boost or amplify the excitation data signals and send them to the spectrometer 304. The spectrometer 304 can send the excitation data to the computer 302 for storage, analysis, and image construction. The computer 302 can combine multiple stored excitation data signals to create an image, for example.

From the spectrometer 304, signals can also be relayed to the RF transmission coils 310 via an RF power amplifier 306.

Figure 9:
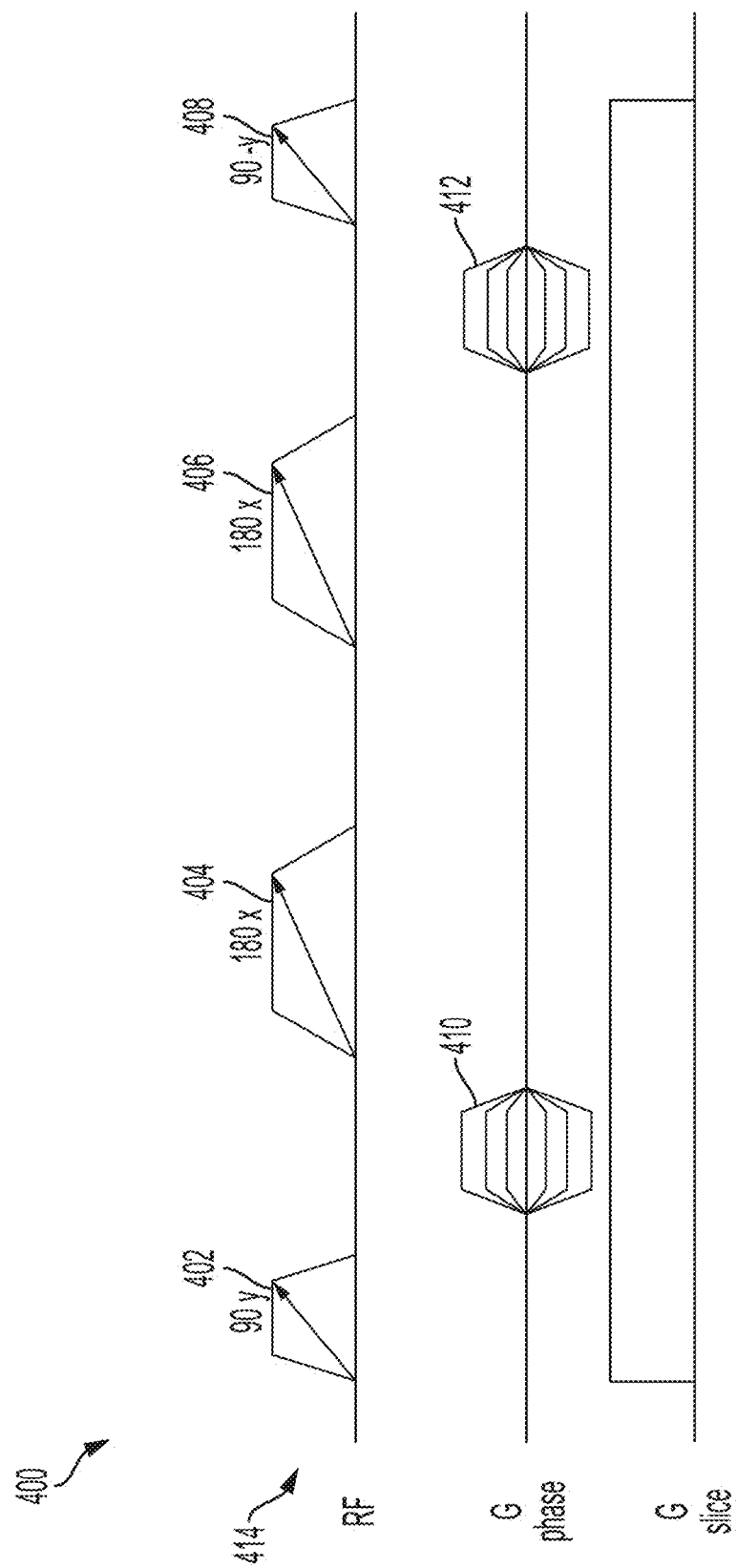
FIG. 9 is a diagram showing a sweeping frequency pulse sequence for DEFT, according to various aspects of the present disclosure.

FIG. 9 shows a diagram 400 of an example sweeping frequency pulse sequence 414 for DEFT through time. The pulses along the line labeled RF are frequency sweep RF pulses having a changing frequency for the duration of the RF pulse. The phase encoding gradient along the line labeled G phase represents the phase encodes. The slice selection gradient along the line labeled G slice represents the permanent inherent gradient in the magnetic field.

The first RF pulse 402 in the sweeping frequency DEFT pulse sequence 414 is an excitation pulse. The first RF pulse 402 can be a 90 degree sweeping frequency pulse along the Y axis (FIG. 1) at a sweep rate and for a pulse duration. The first RF pulse 402 in the sweeping frequency DEFT pulse sequence 414 can increase the slice selection gradient to a constant value at the start of the first RF pulse 402, and the slice selection gradient can remain at that constant value for the entire sweeping frequency pulse sequence 414. This slice selection gradient can therefore be a temporarily applied electromagnetic gradient or a permanent always-on gradient. The first RF pulse 402 is configured to generate an electromagnetic field, which can rotate the magnetization from the permanent magnet assembly 308 in the MRI scanner (i.e. magnetization from the inherent gradient magnetic field B0) 90 degrees to extend in a transverse plane and in a first direction for the duration of the first RF pulse 402. A first phase encoding gradient or pulse 410 occurs after the first RF pulse 402.

The second RF pulse 404 in the sweeping frequency DEFT pulse sequence 414 is a refocusing pulse. The second RF pulse 404 can be a 180 degree sweeping frequency pulse along the X axis (FIG. 1) at a sweep rate and for a pulse duration. The sweep rate of the second RF pulse 404 can be the same as the first RF pulse 402. In another aspect, the sweep rate of the second RF pulse 404 can be different from the first RF pulse 402. The second RF pulse 404 is configured to generate an electromagnetic field, which can invert the magnetization 180 degrees to extend in the opposite direction from direction during the first RF pulse 402 for the duration of the second RF pulse 404. The second RF pulse 404 may be used to refocus the phase dispersion accumulated during its time in that plane.

The third RF pulse 406 in the sweeping frequency DEFT pulse sequence 414 is a second refocusing pulse. The third RF pulse 406 can be another 180 degree sweeping frequency pulse along the X axis (FIG. 1) at a sweep rate and for a pulse duration. The sweep rate of the third RF pulse 404 can be the same as the first RF pulse 402 and/or second RF pulse 404. The third RF pulse 406 is configured to generate an electromagnetic field, which can invert the magnetization 180 degrees to extend in the opposite direction from the direction during the second RF pulse 404 for the duration of the third RF pulse 406. The third RF pulse 406 may also be used to refocus the phase dispersion accumulated during its time in that plane. A second phase encoding gradient or pulse 412 occurs after the third RF pulse 406.

The fourth RF pulse 408 in the sweeping frequency DEFT pulse sequence 414 is a second excitation pulse. The fourth RF pulse 408 can be a 90 degree sweeping frequency pulse along the -Y axis (FIG. 1) at a sweep rate and for a sweep duration. The sweep rate of the fourth RF pulse 408 is less than the sweep rate of the third RF pulse 406 and/or the second RF pulse 404. In various aspects, the sweep rate of the fourth RF pulse 408 can be half the sweep rate of the third RF pulse 406 and half the sweep rate of the second RF pulse 406. For example, the sweep rates of the second RF pulse 404 and the third RF pulse 406 can be the same. The fourth RF pulse 408 is configured to generate an electromagnetic field, which can rotate the magnetization 90 degrees to return the magnetization into alignment with the primary magnetic field axis B0, which extends from the permanent magnet assembly 308 into the field of view 312.

As described herein, the sweeping frequency DEFT pulse sequence 414 can consist of the four RF pulses 402, 404, 406, and 408 described herein. In other aspects, the sweep frequency pulse sequence can have more than four RF pulses. For example, sweeping frequency DEFT pulse sequences having six pulses are also contemplated.

The sweep rates for the first RF pulse 402, the second RF pulse 404, and the third RF pulse 406 are the same. In other instances, at least one of the sweep rates for the first RF pulse 402, the second RF pulse 404, and the third RF pulse 406 can be different than the others. Typical sweep rates include 200 KHz/ms, 100 KHz/ms, 80 KHz/ms, 40 KHz/ms, 20 KHz/ms, 13 KHz/ms, 10 KHz/ms, 5 KHz/ms, for example.

Moreover, the pulse duration for the first RF pulse 402 and the fourth RF pulse 408 are the same, and the pulse duration for the second RF pulse 404 and the third RF pulse 406 are the same. The pulse duration for the second RF pulse 404 and the third RF pulse 406 is greater than the pulse duration for the first RF pulse 402 and the fourth RF pulse 408. In other instances, the pulse duration for at least one of the first RF pulse 402, the second RF pulse 404, the third RF pulse 406, and the fourth RF pulse 408 can be different than the others. In still other instances, all the pulse durations in the sweeping frequency DEFT pulse sequence can be the same.

With respect to FIG. 9, the DEFT pulse sequence 414 includes four sequential pulses directed along the following axes—the Y axis for the first pulse 402, the X axis for the second pulse 404, the X axis again for the third pulse 406, and the −Y axis for the fourth pulse 408. In other instances, the DEFT pulse sequence 414 can four sequential pulses directed along the following axes—the X axis for the first pulse 402, the Y axis for the second pulse 404, the Y axis again for the third pulse 406, and the −X axis for the fourth pulse 408. Similarly, the magnetization will be returned to the Z axis from the transverse plane with the fourth pulse 408. Alternatively, in an echo train experiment, there would be more than two Y axis pulses between the X axis pulses.

Figure 10:
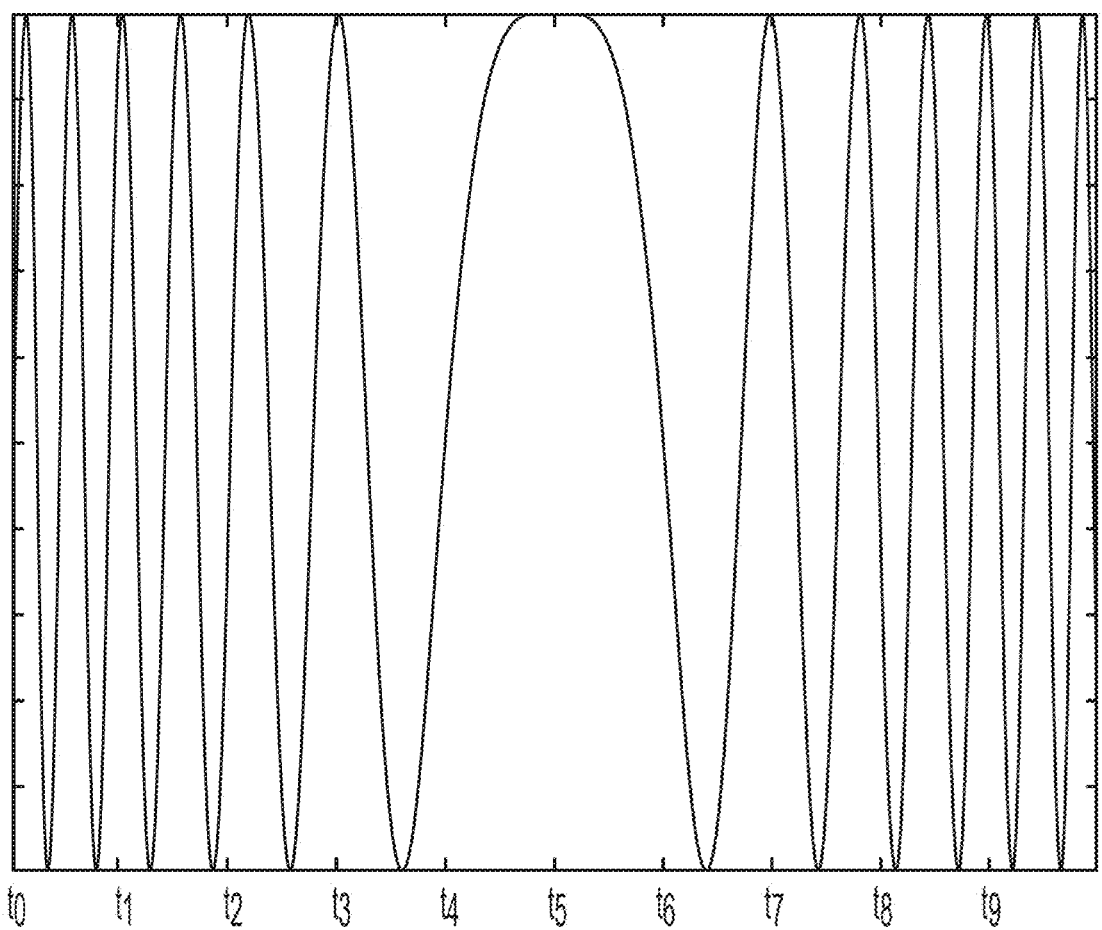
FIG. 10 is a representative graph of a sweeping frequency pulse, according to various aspects of the present disclosure.

Referring now to FIG. 10, a representative graph 500 of a sweeping frequency pulse or chirp pulse is shown. The pulse frequency in the graph 500 can be a negative-to-positive frequency increase. The frequency of a chirp pulse can vary from a minimum (lowest) desired frequency to a maximum (highest) desired frequency. In other instances, the sweeping frequency pulse can sweep from high to low. In certain instances, the frequency sweep can be a linear sweep; the sweep rate can be constant. In other instances, the rate can be a hyperbolic secant sweeps, for example.

The sweep rate of the pulse is the difference between the highest frequency and lowest frequency in the pulse divided by the time required to go between the highest frequency and the lowest frequency. In one aspect, the frequency range that is covered by the sweeping frequency pulses used in the sweeping frequency pulse sequence 414 may be from −20 KHz to 20 KHz, i.e. a 40 KHz range, with a center frequency that varies slab to slab. For example, a slab could be centered at 2.62 MHz, 2.75 MHz, 2.65 MHz, 2.72 MHz, 2.79 MHz, 2.69 MHz, and so on. For a slab centered at 2.62 MHz, the chirp pulse would sweep from 2.60 MHz to 2.64 MHz, i.e. a 40 KHz range. In other aspects of the present disclosure, bandwidths as low as 10 KHz to as high as 200 KHz may be used in the frequency sweep pulse. Moreover, the sweep range can be less than 40 KHz in various instances. The slab may also be centered at a different frequency, which can be any frequency within the range specified, for example.

Figure 11:
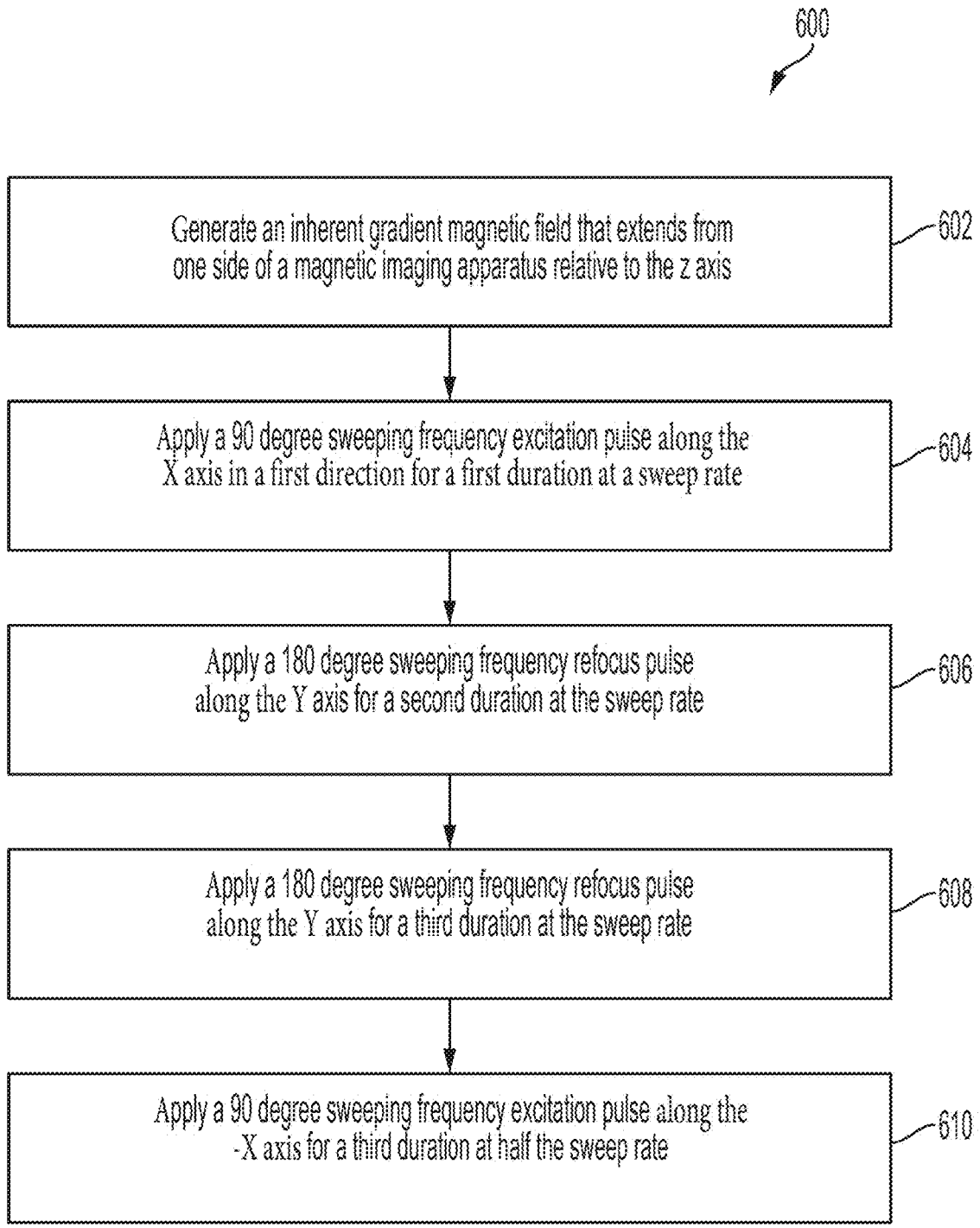
FIG. 11 is a flow diagram of a sweeping frequency pulse sequence for DEFT, according to various aspects of the present disclosure.

Referring now to FIG. 11, a flow diagram of a sweeping frequency DEFT pulse sequence 600 is shown. The process begins at 602, in which an inherent gradient magnetic field is generated that extends from one side of a magnetic imaging apparatus relative to the Z axis (FIG. 1). A permanent magnet of the magnetic imaging apparatus creates the inherent gradient magnetic field that extends perpendicularly away from the magnetic imaging apparatus along a Z axis, for example. At 604, a 90 degree sweeping frequency excitation pulse is applied, which is configured to generate an electromagnetic field extending along the X axis for a first duration and at a sweep rate. The electromagnetic field is configured to alter the magnetization resulting from the inherent gradient magnetic field and to rotate that magnetization into a transverse plane.

Then, at 606, a 180 degree sweeping frequency refocus pulse is applied, which is configured to generate an electromagnetic field along the Y axis to invert the magnetization of the inherent gradient magnetic field in the transverse plane. The 180 degree sweeping frequency refocusing pulse at 606 defines a second duration and the same sweep rate. Next, at 608, a second 180 degree sweeping frequency refocus pulse is applied, which is configured to generate an electromagnetic field along the Y axis in the opposite direction from the pulse at 606 to invert the magnetization of the inherent gradient magnetic field in the transverse plane. The 180 degree sweeping frequency refocusing pulse at 608 defines a third duration and the same sweep rate. At 610, a second 90 degree sweeping frequency excitation pulse is applied, which is configured to generate an electromagnetic field extending along the −X axis for a fourth duration at half the sweep rate of the other pulses at 604, 606, and 608. This pulse at 610 is configured return the magnetization from the inherent gradient magnetic field back to the Z axis from the transverse plane.

When a DEFT pulse sequence uses conventional single frequency or "hard" pulses, returning magnetization back onto the Z axis is relatively simple. The spin ensemble can have a well-defined net phase for the entirety of the sequence. If the spin ensemble accumulates any phase during an RF pulse, it is typically spatially-dependent and, thus, can be refocused with either a spin echo or a refocusing gradient pulse. On the other hand, for spin ensembles affected by frequency sweep pulses, during the frequency sweep pulse, the spin ensemble will acquire a frequency-dependent quadratic phase. Such a frequency-dependent quadratic phase generally cannot be re-wound except with another frequency sweep pulse having double the sweep rate of the first frequency sweep pulse. This can make the use of a frequency sweep pulse as a driven equilibrium pulse difficult.

Chirped echo train experiments are known for having echoes with alternating phase characteristics. If the refocusing pulses in the chirped echo train have half the sweep rate of the excitation pulse in the beginning of the train, then the echoes it produces can either be a spin echo or a spectral echo. For example, some echoes produced can be spin echoes, while the other echoes produced can be spectral echoes. So, in a frequency sweep DEFT sequence, which has two frequency sweep refocusing pulses, the second echo produced will be a spectral echo. This can be problematic because a spectral echo is unlike a spin echo in ways that make it difficult to place it back onto the Z axis. Unlike a spin echo, a spectral echo is a collection of echoes where every different frequency in the spin ensemble refocuses at a different time. The magnetization during this spectral echo can also contain a quadratic phase. This means that the spin ensemble can refocus during different times and also point in different directions along the X-Y plane. So, to place the spins of a spectral echo back onto the Z axis, the driven equilibrium pulse can be both orthogonal to the echo when it refocuses and in the appropriate orientation/direction to place it along +Z instead of −Z.

Frequency sweep DEFT pulse sequences can provide the benefits of the broader bandwidth and less sensitivity to the inhomogeneity of a single-sided MRI scanner. After the first excitation pulse, the spins will be excited in a frequency dependent time order, which means some spins can already be excited and start dephasing while others will be excited later. After the first excitation pulse, e.g. a 90 degree frequency sweep pulse, spins have phase that depend, for example, on frequency and local inhomogeneity. Then, a first refocusing pulse, e.g. a 180 degree frequency sweep pulse, can be used to refocus the phase of the first excitation pulse. It can be designed to follow the frequency dependent time order of the first excitation pulse. Therefore, all spins can be in phase again at the same time at some time after the first refocusing pulse. Afterwards, the spins can begin to dephase again, but can be refocused with a second refocusing pulse, e.g. another 180 degree frequency sweep pulse, resulting in a spin ensemble with a quadratic phase across it. This quadratic phase can be matched with a second excitation pulse, e.g. a 90 degree frequency sweep pulse having a sweep rate that is less than the sweep rate of the first and second refocusing pulses. In at least one instance, the sweep rate of the second excitation pulse can be half the sweep rate of the first and second refocusing pulses. By setting the sweep rate in this way, the quadratic phase of the signal is compensated, allowing the entire spin ensemble to be returned to the Z axis.

EXAMPLES

Various aspects of the subject matter described herein are set out in the following numbered examples.

Example 1—A method for transmitting radio frequency pulses for a single-sided magnetic imaging apparatus, wherein an inherent gradient magnetic field extends from the magnetic imaging apparatus relative to a first axis into the field of view, and wherein the method comprises: applying a first sweeping frequency pulse having a first duration and a first sweep rate, wherein the first sweeping frequency pulse defines an X axis; applying a second sweeping frequency pulse having a second duration and a second sweep rate, wherein the second sweeping frequency pulse defines a first Y axis; applying a third sweeping frequency pulse having a third duration and a third sweep rate, wherein the third sweeping frequency pulse defines a second Y axis; and applying a fourth sweeping frequency pulse having a fourth duration and a fourth sweep rate, wherein the fourth sweeping frequency pulse defines a −X axis, and wherein the fourth sweep rate is less than the third sweep rate.

Example 2—The method of Example 1, wherein the first sweeping frequency pulse comprises a first 90 degree pulse configured to rotate the magnetization to a transverse plane for the first duration.

Example 3—The method of any of Examples 1 and 2, wherein the second sweeping frequency pulse comprises a first 180 degree pulse configured to invert the magnetization to rewind any phase accumulated during the time it spends in the transverse plane.

Example 4—The method of any of Examples 1, 2, and 3, wherein the third sweeping frequency pulse comprises a second 180 degree pulse configured to invert the magnetization to rewind any phase accumulated during the time it spends in the transverse plane.

Example 5—The method of any of Examples 1, 2, 3, and 4, wherein the fourth sweeping frequency pulse comprises a second 90 degree pulse configured to rotate the magnetization back to the first axis.

Example 6—The method of any of Examples 1, 2, 3, 4, and 5, wherein the sweep rates comprise linear rates.

Example 7—The method of any of Examples 1, 2, 3, 4, 5, and 6, wherein the fourth sweep rate is half the third sweep rate.

Example 8—The method of any of Examples 1, 2, 3, 4, 5, 6, and 7, wherein the sweep rate of each pulse is constant.

Example 9—The method of any of Examples 1, 2, 3, 4, 5, 6, 7, and 8, wherein the first sweep rate is fixed and increases the frequency of the radio frequency pulse from negative to positive.

Example 10—The method of any of Examples 1, 2, 3, 4, 5, 6, 7, 8, and 9, wherein at least two of the first duration, the second duration, the third duration, and the fourth duration are the same.

Example 11—The method of any of Examples 1, 2, 3, 4, 5, 6, 7, 8, 9, and 10, wherein at least two of the first sweep rate, the second sweep rate, third sweep rate, and the fourth sweep rate are the same.

Example 12—The method of any of Examples 1, 2, 3, 4, 5, 6, 7, 8, 9, 10, and 11, wherein the first sweeping frequency pulse comprises a first excitation pulse.

Example 13—The method of any of Examples 1, 2, 3, 4, 5, 6, 7, 8, 9, 10, 11, and 12, wherein the second sweeping frequency pulse comprises a first refocusing pulse.

Example 14—The method of any of Examples 1, 2, 3, 4, 5, 6, 7, 8, 9, 10, 11, 12, and 13, wherein the third sweeping frequency pulse comprises a second refocusing pulse.

Example 15—The method of any of Examples 1, 2, 3, 4, 5, 6, 7, 8, 9, 10, 11, 12, 13, and 14, wherein the fourth sweeping frequency pulse comprises a second excitation pulse.

Example 16—The method of any of Examples 1, 2, 3, 4, 5, 6, 7, 8, 9, 10, 11, 12, 13, 14, and 15, wherein the first frequency sweeping pulse, the second frequency sweeping pulse, the third frequency sweeping pulse, and the fourth frequency sweeping pulse define a frequency of between 1 Megahertz and 21 Megahertz.

Example 17—The method of any of Examples 1, 2, 3, 4, 5, 6, 7, 8, 9, 10, 11, 12, 13, 14, 15, and 16, wherein the magnetic field strength in the field of view is less than 1 Tesla.

Example 18—The method of any of Examples 1, 2, 3, 4, 5, 6, 7, 8, 9, 10, 11, 12, 13, 14, 15, 16, and 17, wherein the inhomogeneity of the magnetic field is between 200 ppm and 200,000 parts per million.

Example 19—A magnetic imaging apparatus, comprising: a permanent magnet comprising a face; a gradient coil set; an electromagnet; a radio frequency coil, wherein an inherent gradient magnetic field extends from the magnetic imaging apparatus relative to a first axis into the field of view, wherein the first axis is perpendicular to the face of the permanent magnet; and a control circuit configured to control the radio frequency coil to: apply a first sweeping frequency pulse having a first duration and a first sweep rate, wherein the first sweeping frequency pulse defines a second axis that is orthogonal to the first axis; apply a second sweeping frequency pulse having a second duration and a second sweep rate, wherein the second sweeping frequency pulse defines a third axis that is orthogonal to the first axis and to the second axis; apply a third sweeping frequency pulse having a third duration and a third sweep rate, wherein the third sweeping frequency pulse defines the third axis; and apply a fourth sweeping frequency pulse having a fourth duration and a fourth sweep rate, wherein the fourth sweeping frequency pulse defines the negative second axis, wherein the fourth sweep rate is less than the third sweep rate.

Example 20—The magnetic imaging apparatus of Example 19, wherein the first sweeping frequency pulse comprises a 90 degree pulse configured to rotate the magnetization to a transverse plane for the first duration.

Example 21—The magnetic imaging apparatus of any of Examples 19 and 20, wherein the second sweeping frequency pulse comprises a first 180 degree pulse configured to invert the magnetization to rewind any accumulated phase.

Example 22—The magnetic imaging apparatus of any of Examples 19, 20, and 21, wherein the third sweeping frequency pulse comprises a second 180 degree pulse configured to invert the magnetization to rewind any accumulated phase.

Example 23—The magnetic imaging apparatus of any of Examples 19, 20, 21, and 22, wherein the fourth sweeping frequency pulse comprises a second 90 degree pulse configured to rotate the magnetization back to the first axis.

Example 24—The magnetic imaging apparatus of any of Examples 19, 20, 21, 22, and 23, wherein the first sweeping frequency pulse defines an X axis, wherein the second sweeping frequency pulse and the third sweeping frequency pulse define a Y axis, and wherein the fourth sweeping frequency pulse defines a −X axis.

Example 25—The magnetic imaging apparatus of any of Examples 19, 20, 21, 22, 23, and 24, wherein the fourth sweep rate is half the third sweep rate.

Example 26—The magnetic imaging apparatus of any of Examples 19, 20, 21, 22, 23, 24, and 25, wherein the sweep rates are constant throughout each pulse.

Example 27—The magnetic imaging apparatus of any of Examples 19, 20, 21, 22, 23, 24, 25, and 26, wherein the first frequency sweep rate increases the frequency from high to low.

Example 28—The magnetic imaging apparatus of any of Examples 19, 20, 21, 22, 23, 24, 25, 26, and 27, wherein at least two of the first duration, the second duration, the third duration, and the fourth duration are the same.

Example 29—The magnetic imaging apparatus of any of Examples 19, 20, 21, 22, 23, 24, 25, 26, 27, and 28, wherein at least two of the first sweep rate, the second sweep rate, third sweep rate, and the fourth sweep rate are the same.

Example 30—The magnetic imaging apparatus of any of Examples 19, 20, 21, 22, 23, 24, 25, 26, 27, 28, and 29, wherein the first sweeping frequency pulse comprises a first excitation pulse.

Example 31—The magnetic imaging apparatus of any of Examples 19, 20, 21, 22, 23, 24, 25, 26, 27, 28, 29, and 30, wherein the second sweeping frequency pulse comprises a first refocusing pulse.

Example 32—The magnetic imaging apparatus of any of Examples 19, 20, 21, 22, 23, 24, 25, 26, 27, 28, 29, 30, and 31, wherein the third sweeping frequency pulse comprises a second refocusing pulse.

Example 33—The magnetic imaging apparatus of any of Examples 19, 20, 21, 22, 23, 24, 25, 26, 27, 28, 29, 30, 31, and 32, wherein the fourth sweeping frequency pulse comprises a second excitation pulse.

Example 34—The magnetic imaging apparatus of any of Examples 19, 20, 21, 22, 23, 24, 25, 26, 27, 28, 29, 30, 31, 32, and 33, wherein the radio frequency coil is configured to transmit pulses having a frequency between 1 Megahertz and 21 Megahertz.

Example 35—The magnetic imaging apparatus of any of Examples 19, 20, 21, 22, 23, 24, 25, 26, 27, 28, 29, 30, 31, 32, 33, and 34, wherein the magnetic field strength in the field of view is less than 1 Tesla.

Example 36—The magnetic imaging apparatus of any of Examples 19, 20, 21, 22, 23, 24, 25, 26, 27, 28, 29, 30, 31, 32, 33, 34, and 35, wherein the inhomogeneity of the magnetic field is between 200 ppm and 200,000 ppm.

Example 37—The magnetic imaging apparatus of any of Examples, 19, 20, 21, 22, 23, 24, 25, 26, 27, 28, 29, 30, 31, 32, 33, 34, 45, and 36, wherein the radio frequency coil comprises a radio frequency transmission coil and a radio frequency reception coil.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion, or housing, of a surgical instrument. The term "proximal" refers to the portion closest to the clinician and/or to the robotic arm and the term "distal" refers to the portion located away from the clinician and/or from the robotic arm. It will be further appreciated that, for convenience and clarity, spatial terms such as "vertical", "horizontal", "up", and "down" may be used herein with respect to the drawings. However, robotic surgical tools are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method for transmitting radio frequency pulses for a single-sided magnetic imaging apparatus, wherein an inherent gradient magnetic field extends from the magnetic imaging apparatus relative to a first axis into the field of view, and wherein the method comprises:

applying a first sweeping frequency pulse having a first duration and a first sweep rate, wherein the first sweeping frequency pulse defines an X axis, wherein the first sweeping frequency pulse comprises a first 90 degree pulse configured to rotate the magnetization to a transverse plane for the first duration;
applying a second sweeping frequency pulse having a second duration and a second sweep rate, wherein the second sweeping frequency pulse defines a first Y axis;
applying a third sweeping frequency pulse having a third duration and a third sweep rate, wherein the third sweeping frequency pulse defines a second Y axis; and
applying a fourth sweeping frequency pulse having a fourth duration and a fourth sweep rate, wherein the fourth sweeping frequency pulse defines a −X axis, wherein the fourth sweeping frequency pulse comprises a second 90 degree pulse configured to rotate the magnetization back to the first axis, and wherein the fourth sweep rate is less than the third sweep rate.

2. The method of claim 1, wherein the second sweeping frequency pulse comprises a first 180 degree pulse configured to invert the magnetization to rewind any phase accumulated during the time it spends in the transverse plane, and wherein the third sweeping frequency pulse comprises a second 180 degree pulse configured to invert the magnetization to rewind any phase accumulated during the time it spends in the transverse plane.

3. The method of claim 1, wherein the sweep rates comprise linear rates.

4. The method of claim 1, wherein the fourth sweep rate is half the third sweep rate.

5. The method of claim 1, wherein the sweep rate of each pulse is constant.

6. The method of claim 1, wherein the first sweep rate is fixed and increases the frequency of the radio frequency pulse from negative to positive.

7. The method of claim 1, wherein at least two of the first duration, the second duration, the third duration, and the fourth duration are the same.

8. The method of claim 1, wherein at least two of the first sweep rate, the second sweep rate, third sweep rate, and the fourth sweep rate are the same.

9. The method of claim 1, wherein the first sweeping frequency pulse comprises a first excitation pulse, wherein the second sweeping frequency pulse comprises a first refocusing pulse, wherein the third sweeping frequency pulse comprises a second refocusing pulse, and wherein the fourth sweeping frequency pulse comprises a second excitation pulse.

10. The method of claim 1, wherein the first frequency sweeping pulse, the second frequency sweeping pulse, the third frequency sweeping pulse, and the fourth frequency sweeping pulse define a frequency of between 1 Megahertz and 21 Megahertz.

11. The method of claim 1, wherein the magnetic field strength in the field of view is less than 1 Tesla, and wherein the inhomogeneity of the magnetic field is between 200 ppm and 200,000 parts per million.

12. A magnetic imaging apparatus, comprising:
a permanent magnet comprising a face;
a gradient coil set;
an electromagnet;
a radio frequency coil, wherein an inherent gradient magnetic field extends from the magnetic imaging apparatus relative to a first axis into the field of view, wherein the first axis is perpendicular to the face of the permanent magnet; and
a control circuit configured to control the radio frequency coil to:
apply a first sweeping frequency pulse having a first duration and a first sweep rate, wherein the first sweeping frequency pulse defines a second axis that is orthogonal to the first axis, wherein the first sweeping frequency pulse comprises a 90 degree pulse configured to rotate the magnetization to a transverse plane for the first duration;
apply a second sweeping frequency pulse having a second duration and a second sweep rate, wherein the second sweeping frequency pulse defines a third axis that is orthogonal to the first axis and to the second axis;
apply a third sweeping frequency pulse having a third duration and a third sweep rate, wherein the third sweeping frequency pulse defines the third axis; and
apply a fourth sweeping frequency pulse having a fourth duration and a fourth sweep rate, wherein the fourth sweeping frequency pulse defines the negative second axis, wherein the fourth sweeping frequency pulse comprises a second 90 degree pulse configured to rotate the magnetization back to the first axis, and wherein the fourth sweep rate is less than the third sweep rate.

13. The magnetic imaging apparatus of claim 12, wherein the second sweeping frequency pulse comprises a first 180 degree pulse configured to invert the magnetization to rewind any accumulated phase, and wherein the third sweeping frequency pulse comprises a second 180 degree pulse configured to invert the magnetization to rewind any accumulated phase.

14. The magnetic imaging apparatus of claim 12, wherein the first sweeping frequency pulse defines an X axis, wherein the second sweeping frequency pulse and the third sweeping frequency pulse define a Y axis, and wherein the fourth sweeping frequency pulse defines a −X axis.

15. The magnetic imaging apparatus of claim 12, wherein the fourth sweep rate is half the third sweep rate.

16. The magnetic imaging apparatus of claim 12, wherein the sweep rates are constant throughout each pulse.

17. The magnetic imaging apparatus of claim 16, wherein the first frequency sweep rate increases the frequency from high to low.

18. The magnetic imaging apparatus of claim 12, wherein at least two of the first duration, the second duration, the third duration, and the fourth duration are the same.

19. The magnetic imaging apparatus of claim 12, wherein at least two of the first sweep rate, the second sweep rate, third sweep rate, and the fourth sweep rate are the same.

20. The magnetic imaging apparatus of claim 12, wherein the first sweeping frequency pulse comprises a first excitation pulse, wherein the second sweeping frequency pulse comprises a first refocusing pulse, wherein the third sweeping frequency pulse comprises a second refocusing pulse, and wherein the fourth sweeping frequency pulse comprises a second excitation pulse.

21. The magnetic imaging apparatus of claim 12, wherein the radio frequency coil is configured to transmit pulses having a frequency between 1 Megahertz and 21 Megahertz.

22. The magnetic imaging apparatus of claim 12, wherein the magnetic field strength in the field of view is less than 1 Tesla, and wherein the inhomogeneity of the magnetic field is between 200 ppm and 200,000 ppm.

23. The magnetic imaging apparatus of claim 12, wherein the radio frequency coil comprises a radio frequency transmission coil and a radio frequency reception coil.

* * * * *